United States Patent
Moore et al.

(10) Patent No.: US 10,776,799 B2
(45) Date of Patent: Sep. 15, 2020

(54) SOFTWARE FOR EMERGENCY MEDICAL SERVICES

(71) Applicant: MP Cloud Technologies, Inc., Austin, TX (US)

(72) Inventors: Debra Moore, Austin, TX (US); John Dadey, Austin, TX (US)

(73) Assignee: MP Cloud Technologies, Inc., Austin, TX (US)

( * ) Notice: Subject to any disclaimer, the term of this patent is extended or adjusted under 35 U.S.C. 154(b) by 774 days.

(21) Appl. No.: 15/073,413

(22) Filed: Mar. 17, 2016

(65) Prior Publication Data

US 2016/0342740 A1 Nov. 24, 2016

Related U.S. Application Data

(60) Provisional application No. 62/134,530, filed on Mar. 17, 2015.

(51) Int. Cl.
*G06F 19/00* (2018.01)
*G06Q 30/02* (2012.01)
*G16H 10/60* (2018.01)

(52) U.S. Cl.
CPC ....... *G06Q 30/0202* (2013.01); *G06F 19/328* (2013.01); *G16H 10/60* (2018.01)

(58) Field of Classification Search
USPC ....................................................... 705/2–4
See application file for complete search history.

(56) References Cited

U.S. PATENT DOCUMENTS

| | | | | |
|---|---|---|---|---|
| 5,550,734 A | * | 8/1996 | Tarter | G06Q 10/10 705/2 |
| 7,233,905 B1 | * | 6/2007 | Hutton | G06Q 30/04 705/2 |
| 7,752,096 B2 | * | 7/2010 | Santalo | G06Q 20/102 705/2 |
| 2003/0050794 A1 | * | 3/2003 | Keck | G06Q 50/22 705/2 |
| 2009/0265186 A1 | * | 10/2009 | Tarassenko | G06F 19/3418 705/3 |
| 2011/0093278 A1 | * | 4/2011 | Hutton | G06Q 10/00 705/2 |

(Continued)

OTHER PUBLICATIONS

Millin, Michael G., Lawrence H. Brown, and Brian Schwartz. "EMS provider determinations of necessity for transport and reimbursement for EMS response, medical care, and transport: combined resource document for the National Association of EMS Physicians position statements." Prehospital Emergency Care 15.4 (2011).*

*Primary Examiner* — Mark Holcomb
(74) *Attorney, Agent, or Firm* — Shah IP Law, PLLC; Samar Shah (57) ABSTRACT

The present disclosure describes an emergency medical services (EMS) system that can provide one or more modules that can assist with at least the collection and distribution of either information or services. For example, the EMS system can include a dispatch module that can assist with dispatching emergency medical services, a claims module that can compile claims including information related to emergency medical services provided to a patient, and an income forecasting module that can assist with forecasting the collection of payments associated with claims.

9 Claims, 11 Drawing Sheets

(56) References Cited

U.S. PATENT DOCUMENTS

| | | | | |
|---|---|---|---|---|
| 2011/0281547 A1* | 11/2011 | Cordero | ............... | G08B 27/001 455/404.1 |
| 2012/0290311 A1* | 11/2012 | Tara | ........................ | G01S 19/17 705/2 |
| 2013/0054259 A1* | 2/2013 | Wojtusiak | .............. | G06Q 50/22 705/2 |
| 2014/0108059 A1* | 4/2014 | Ring | ...................... | G06Q 40/08 705/4 |
| 2016/0140299 A1* | 5/2016 | Al Harbi | ................ | G16H 40/20 705/2 |

* cited by examiner

| Eligibility Verification For | | |
|---|---|---|
| Payer | | |
| Name: TN MEDICARE PART 8 (110 - CAHABA) | | Information Receiver |
| Code: 00431 | | |

| Insured/Subscriber Entered | Response | Entered | Response |
|---|---|---|---|
| Name: | | Member Identification Number: | |
| Code: | | HIC Code: | |
| Gender: Female | Female | Social Security Number: | |
| Address: | | Group Plan: | |
| Address2: | | Date Of Death: N/A | |
| City: | | Eligibility Date: 01/09/2015 | |
| State: | | Time of Inquiry: 01/09/2015 09:47:14 | |
| Zip: | | Update  More... | |

Eligibility Verification Status : Valid (Active)

| Benefit | Service | Benefit Type | Benefit Type | Amount | Plan Date | Coverage | Authorization Indicator | In Network |
|---|---|---|---|---|---|---|---|---|
| Non-Covered | Long Term Ca... | Medicare Part A | | | 09/01/2002 | | | |
| ▲ Active Coverage | Health Benefi... | Medicare Part A | Episode | $1,260.00 | 01/01/2015-1... | | | |
| ▲ Deductible | Health Benefi... | Medicare Part A | Episode | $1,216.00 | 01/01/2015-1... | | | |
| ▲ Deductible | Health Benefi... | Medicare Part A | Remaining | $1,260.00 | 01/01/2015-1... | | | |
| ▲ Deductible | Health Benefi... | Medicare Part A | Remaining | $1,216.00 | 01/01/2014-1... | | | |
| ▲ Deductible | Health Benefi... | Medicare Part A | Remaining | $0.00 | 11/18/2014-1... | | | |

| Patient | | Patient # | M004906812 | Patient # | | DOB | | Gender | Female | Last Worked | |
|---|---|---|---|---|---|---|---|---|---|---|---|
| Patient Address | | | | Patient City | DECHERD | Patient State | Tennessee | Patient Zipcode | 37324 | AR Status | |
| Primary Insurer | TN MEDICARE PART B (110-CAHABA) | | | Date of Service | 11/18/2014 | Claim # | 14356666953 | Claim Status | Incomplete | Special | |

Ambulance | Procedure | Notes & Attachments | Account | | | | | | | Demographics | Back To Ops Primary Payer: TN MEDICARE PART B (310- CAHABA) [Insurance] ☑ COB Checked Narrative/HCFA Note ICD-9 Code
[+]

| | Diagnosis Code | Description |   |
|---|---|---|---|
| 1 | 785.50 | Chest pain, unspecified | ✎ ✗ |

Procedure
[+]

| | Procedure | Code | Rate* | Units* | DX1 | DX2 | DX3 | DX4 | M1 | M2 | M3 | M4 | Change | |
|---|---|---|---|---|---|---|---|---|---|---|---|---|---|---|
| | ALS EMERGENCY TRANSPO... | A0423 | $750.92 | 1.0 | 1 | | | | | | | | $750.92 | ✎ ✗ |
| | MILEAGE (PER LOADED MILE) | A0425 | $16.46 | 10.2 | 1 | | | | | | | | | ✎ ✗ |

Count: 2     Total: $918.81

[Validate & Submit] [Delete]

FIG. 11

SOFTWARE FOR EMERGENCY MEDICAL SERVICES

CROSS-REFERENCE TO RELATED APPLICATION

This application claims priority to and the benefit of U.S. Provisional Patent Application No. 62/134,530, filed on Mar. 17, 2015 and titled "Software for Emergency Medical Services," the disclosure of which is incorporated by reference in its entirety.

TECHNICAL FIELD

The subject matter described herein relates to systems and methods for collecting, managing, analyzing, storing and sharing information related to emergency medical services.

BACKGROUND

Emergency medical services (EMS) can include medical care outside of a hospital (e.g., on site of an accident, on the way to a hospital, etc.), transport to medical facilities, and other medical transport for patients with illnesses and injuries which prevent them from transporting themselves. Emergency medical services can be provided by a variety of individuals using a variety of methods. Levels of services available through EMS can fall into three categories, which can include basic life support, advanced life support, and critical care transport.

Emergency medical services can be costly to a patient and it can be difficult for EMS providers to estimate revenues relative to the amounts billed for services. For example, the complexity with billing for medical services (e.g., insurance) and having to write-off billed services due to patients who cannot afford to pay for them can make estimating revenues for EMS providers difficult.

SUMMARY

In one aspect, an emergency medical services (EMS) data processing system is presented. The EMS data processing system includes an EMS database storing EMS data representing emergency medical services related to one or more patients. The EMS data includes, for each patient: a name, one or more medical conditions, at least one address, at least one insurer, and services data associated with each of one or more instances of EMS provided to the patient. The EMS data processing system further includes an EMS computing platform connected with the EMS database.

The EMS computing platform includes a dispatch module connected with the EMS database and a geolocation service providing geolocation data for one or more EMS provider assets that are selectively dispatched to provide EMS to a selected patient. The dispatch module receives user input for the selected patient, and calculates a shortest time of an EMS provider asset to provide the EMS to the patient based on the at least one address. The EMS computing platform further includes a claims module associated with the dispatch module. The claims module generates a claim for the EMS provided to the patient, the claim being based at least in part on the EMS provided to the patient, the one or more medical conditions treated by the EMS, the at least one address, and the at least one insurer associated with the patient. The EMS computing system further includes an income forecasting module that generates a forecast for payment of the claim based on a forecasting model executed by the income forecasting module.

In another aspect, a method of providing emergency medical services (EMS) to a selected patient is disclosed. The method includes the steps of storing EMS data representing emergency medical services related to one or more patients, the EMS data comprising, for each patient: a name, one or more medical conditions, at least one address, at least one insurer, and services data associated with each of one or more instances of EMS provided to the patient;

receiving, by at least one data processor, user input to select the selected patient;

accessing, by at least one data processor, the EMS data from the EMS database for the selected patient;

generating, by at least one data processor, an EMS dispatch for the selected patient, the EMS dispatch comprising providing geolocation data for one or more EMS provider assets that are selectively dispatched to provide the EMS to the selected patient;

generating, by at least one data processor, a claim for the EMS provided to the patient, the claim being based at least in part on the EMS provided to the patient, the one or more medical conditions treated by the EMS, the at least one address, and the at least one insurer associated with the patient; and generating, by at least one data processor, a forecast for payment of the claim based on a forecasting model.

Systems and methods consistent with this approach are described, as well as articles that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Providing emergency medical services (EMS) and managing information and billing related to the services provided can be complex. As such, there is a need to provide a system that can simplify and improve the collection and distribution of information and services related to EMS. The present disclosure describes an EMS system that can provide one or more modules that can assist with at least the collection and distribution of either information or services in an improved and user-friendly way. For example, the EMS system, including any one of the modules, can be web-based, including cloud-based, and can be accessible using a variety of platforms (e.g., mobile devices, tablet computers, PC/laptops, etc.). The modules can be in communication with each other, which can allow the transfer and sharing of data from one module to another and can save time and improve the quality of data and services provided by the EMS system.

The EMS system can also allow interoperability between any one of the modules and/or other third party applications. As such, either data from unrelated applications can be obtained by the EMS system or the system can send data to other unrelated applications in a secure manner. The EMS system can also support two-way data communications between applications and clearinghouse/payers. The EMS system can also be extensible to other third party applications.

Figure 1:
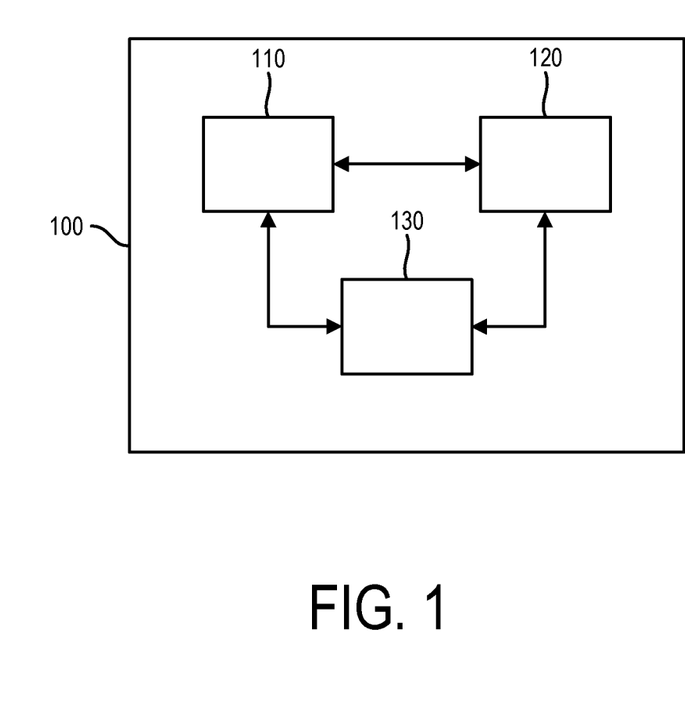
FIG. 1 shows a diagram illustrating features of an EMS system, including a dispatch module, a claims module and an income forecasting module.

FIG. 1 illustrates an example of an EMS system 100 that can include a variety of modules, such as a dispatch module 110, a claims module 120 and an income forecasting module 130. For example, the dispatch module 110 can assist with dispatching medical services, the claims module 120 can compile claims including information related to medical services provided to a patient, and the income forecasting module 130 can assist with forecasting the collection of payments associated with medical services provided, as will be described in greater detail below. The medical services described herein can include either emergency medical services (e.g., ambulance transport from scene of accident to hospital) or non-emergency medical services (e.g., patient transfer between facilities). In addition, even when referred to as emergency medical services or EMS, non-emergency medical services can be included, and vice-versa.

Figure 6:
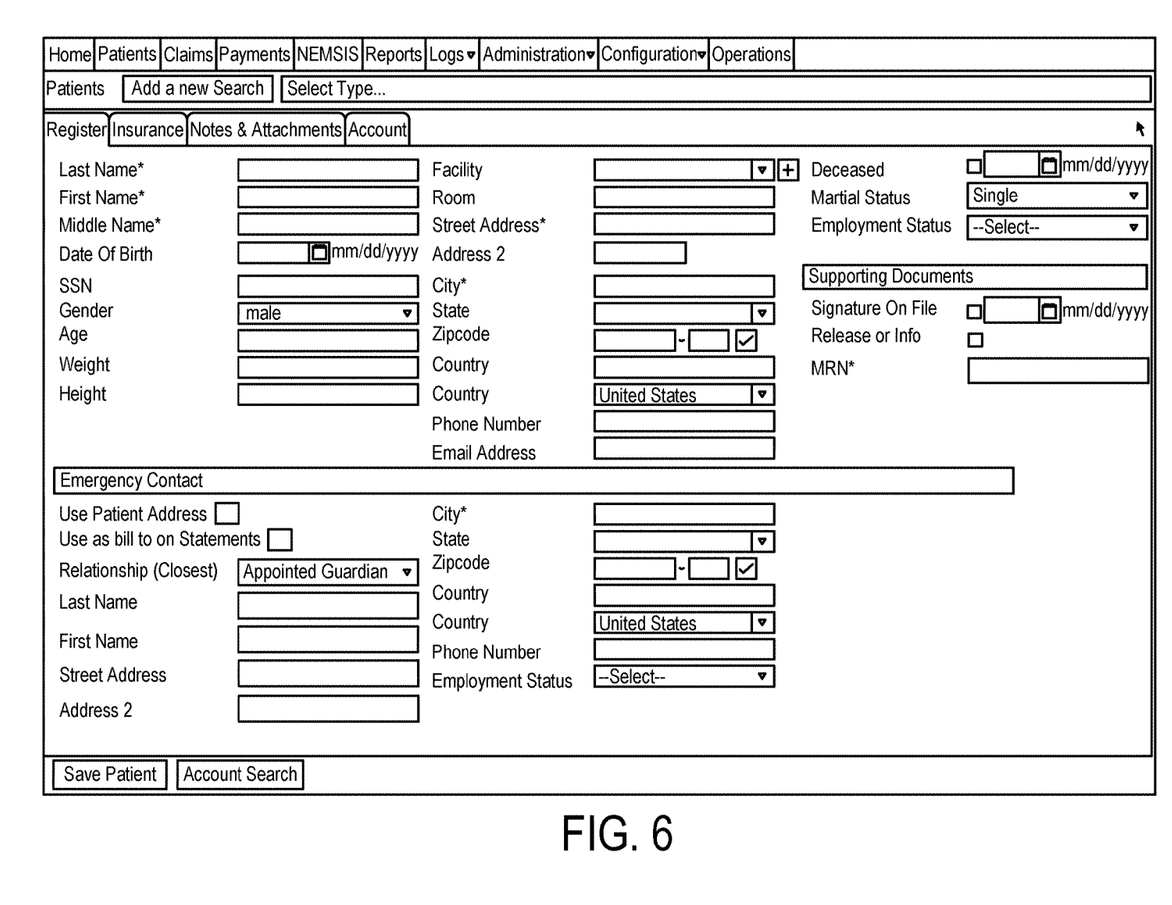
FIG. 6 shows an exemplary user interface for receiving patient information.
Figure 7:
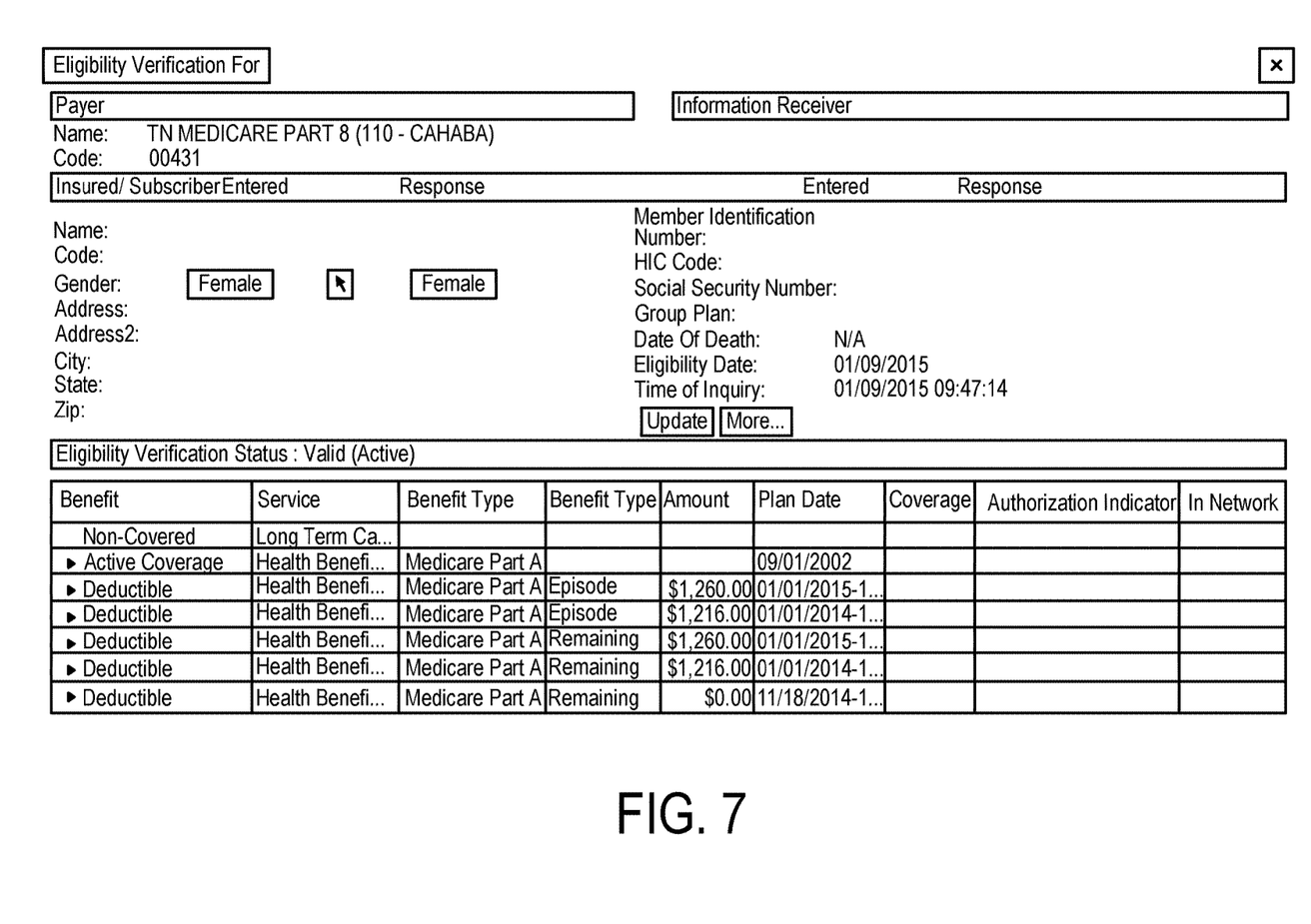
FIG. 7 shows an exemplary user interface for providing an indication of eligibility verification for a specific patient.

FIG. 6 shows an exemplary user interface for receiving, by the EMS system 100, patient information, such as demographic information and other information, such as insurance information, medical history, patient-specific notes, etc. FIG. 7 shows an exemplary user interface for providing an indication of eligibility verification for a specific patient, based at least in part on the patient information, and which could also be based on any EMS being requested for the patient.

Information collected and/or generated by any one of the modules can be shared with other modules. For example, information collected and generated by the dispatch module 110 can be shared with the claims module 120, such as in order to generate a claim. In addition, the income forecasting module 130 can use information collected and generated by the claims module 120, such as in order to forecast collection of payments associated with the claims.

Figure 2:
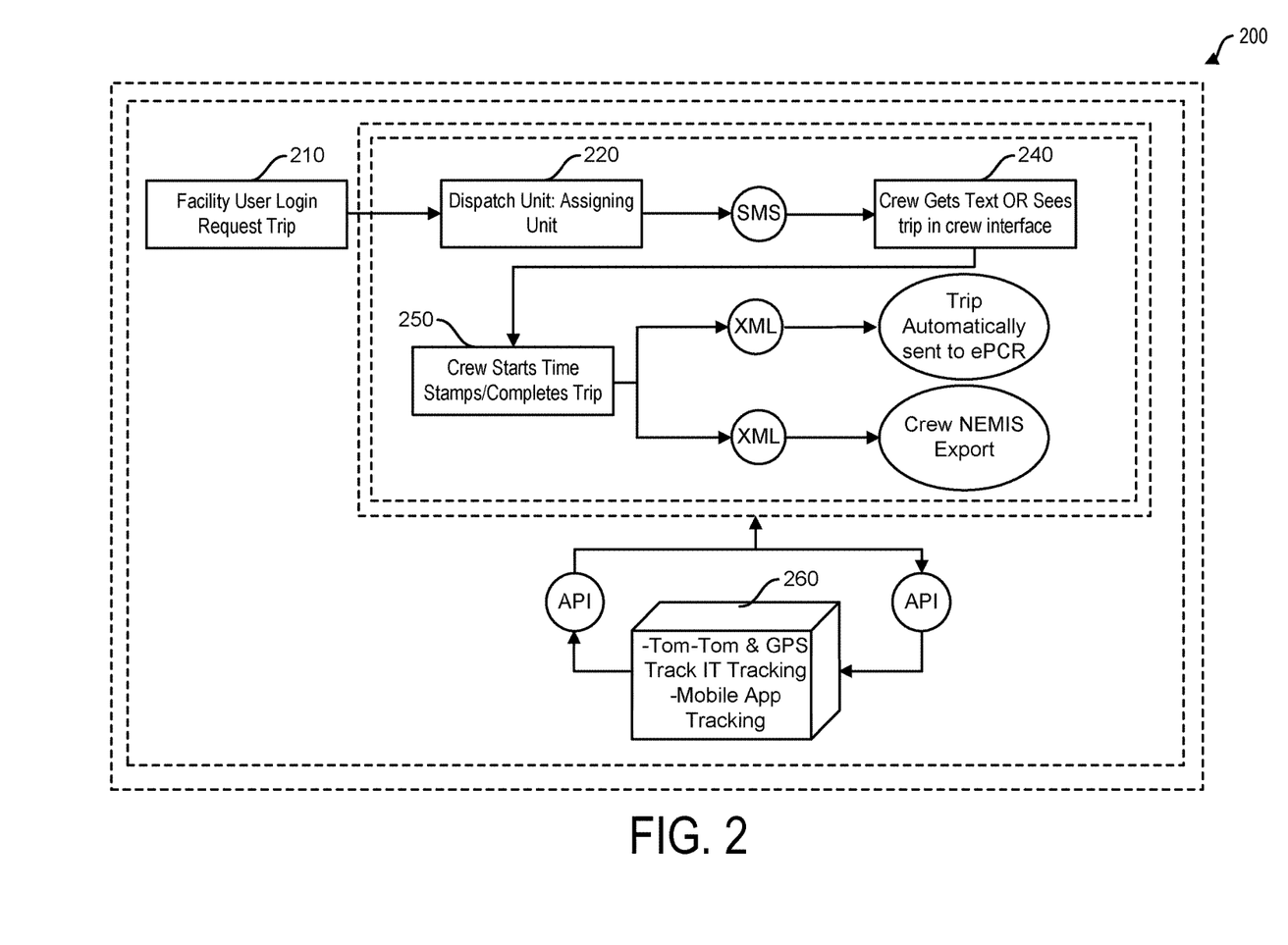
FIG. 2 shows a flow diagram illustrating some processing steps that can be associated with the dispatch module.

FIG. 2 illustrates a diagram showing a dispatch flow diagram 200 associated with the dispatch module 110. For example, at 210, the dispatch module 110 can provide a login interface for a user to login and request medical transport, such as emergency or non-emergency transport services. At 220, a dispatch unit can receive the request and assign a service unit to fulfill the request. The dispatch unit can send a message (e.g., via SMS) to the assigned service unit, which can be received by the service unit, at 240, and allow the service unit to fulfill the request. Alternatively or in addition, the dispatch unit can input information regarding the assigned service unit into the EMS system 100, such as the dispatch module 110, which can be viewed by the assigned service unit in order to allow the service unit to fulfill the request.

At 250, the service unit can provide information to the dispatch module 110 to indicate that the request has been received and/or completed, such as a time stamp. The information entered into and created by the dispatch module 110 can be stored and made available for use with other modules, such as the claims module 120 and/or the forecasting module 130. In addition, at 260, information can be provided to the dispatch module 110 from a variety of sources (e.g., GPS devices, mobile applications, etc.), and this information can also be available to users of the EMS system 100 and/or other modules. The dispatch module 110 can be accessible through the internet and can provide EMS departments and private transport services a cost-effective way to manage their dispatch and tracking of dispatch services, including in at least near real-time.

Figure 8:
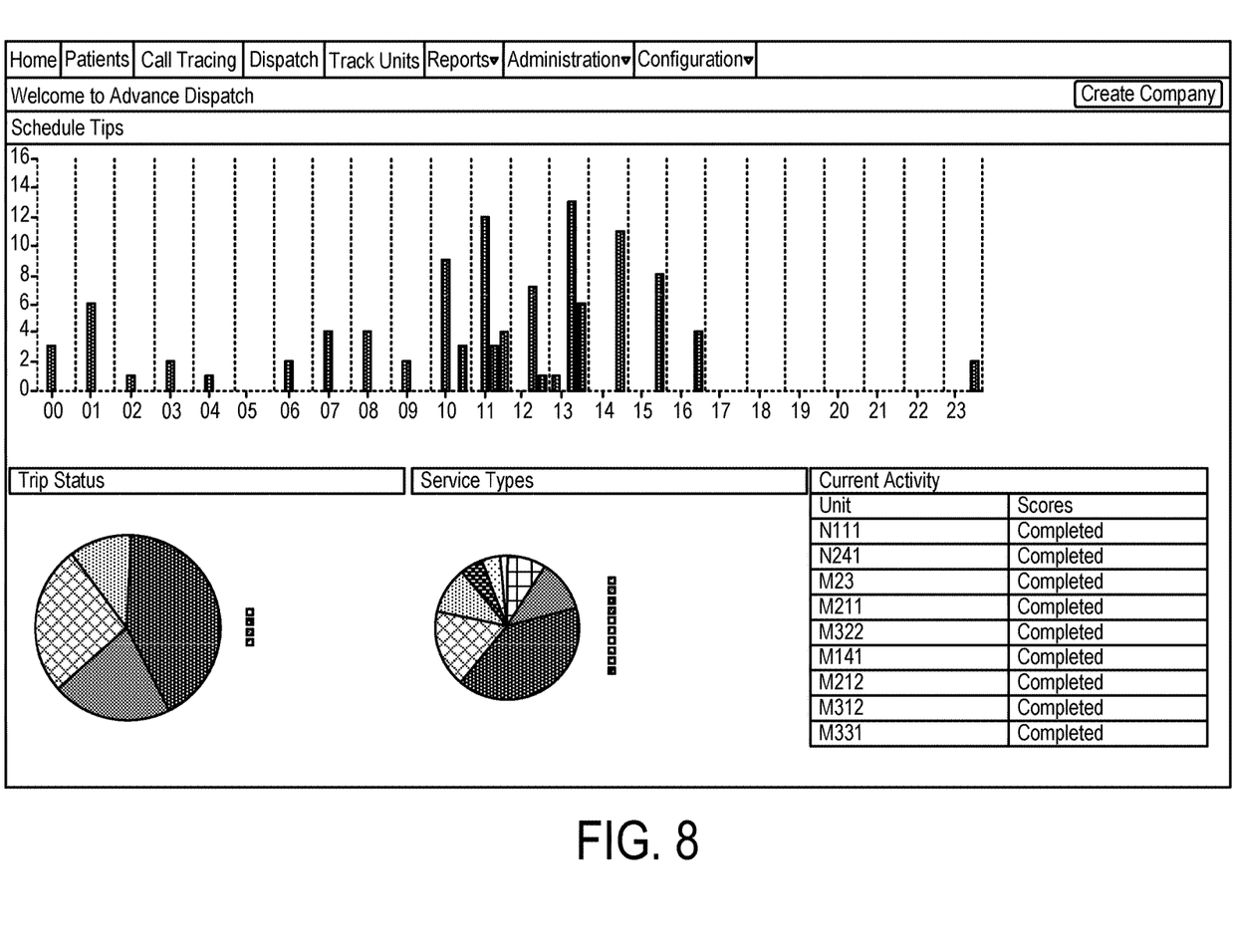
FIG. 8 shows an exemplary user interface of the dispatch module for showing a representation of scheduled, completed, active and unpublished dispatches of EMS.
Figure 9:
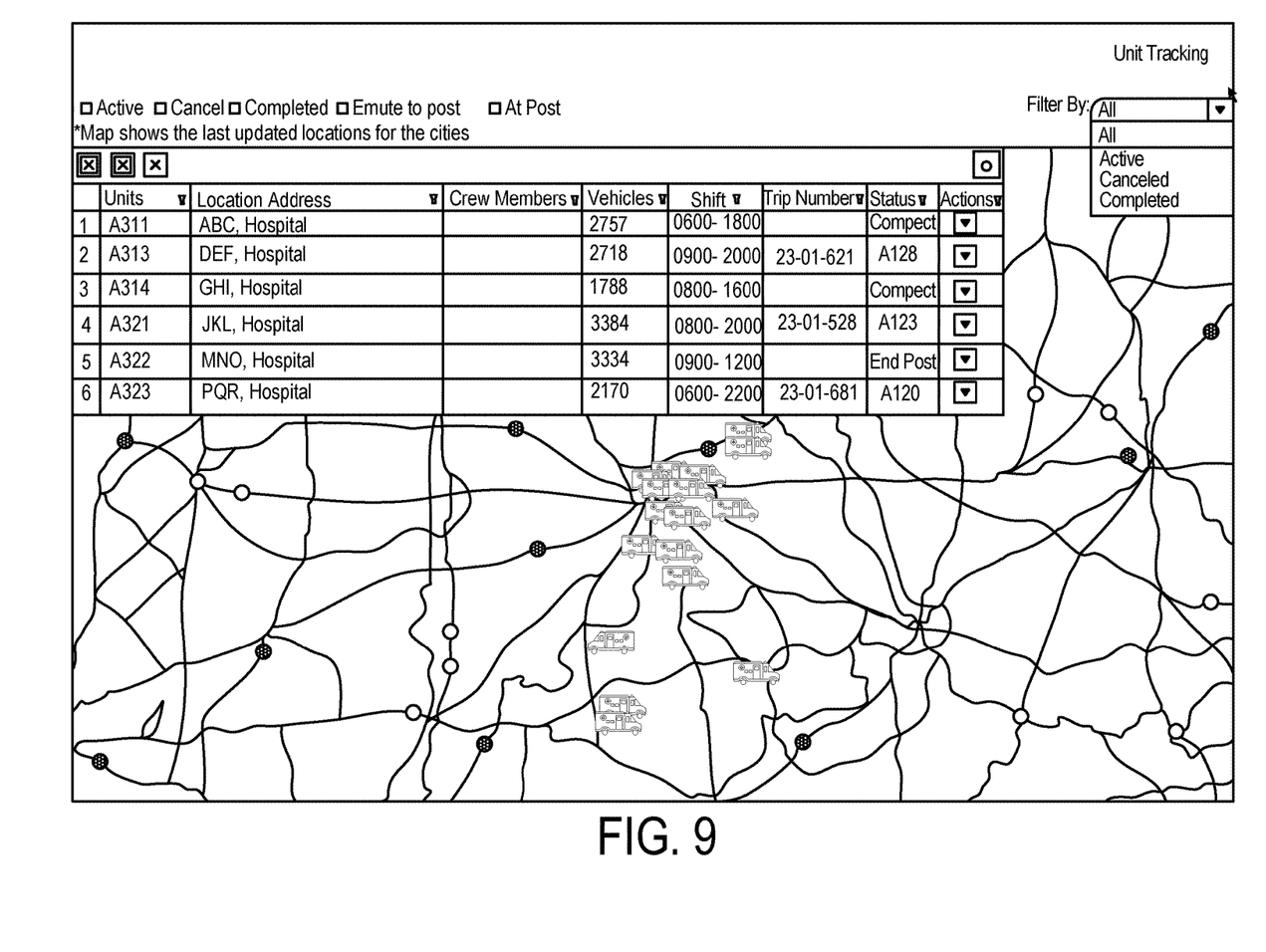
FIG. 9 shows another exemplary user interface of the dispatch module that provides a graphical representation of the current EMS activity in real-time.

FIG. 8 shows an exemplary user interface of the dispatch module 110 for showing a representation of scheduled, completed, active and unpublished dispatches of EMS. The user interface of the dispatch module 110 can also provide a representation of the type of EMS dispatched, as well as a representation of current EMS activity. FIG. 9 shows another exemplary user interface of the dispatch module 110 that provides a graphical representation of the current EMS activity in real-time. In the example shown in FIG. 9, a map is generated, and icons of each active EMS activity is represented on the map, with an ability to provide a user further detail for each EMS activity represented on the user interface.

Figure 3:
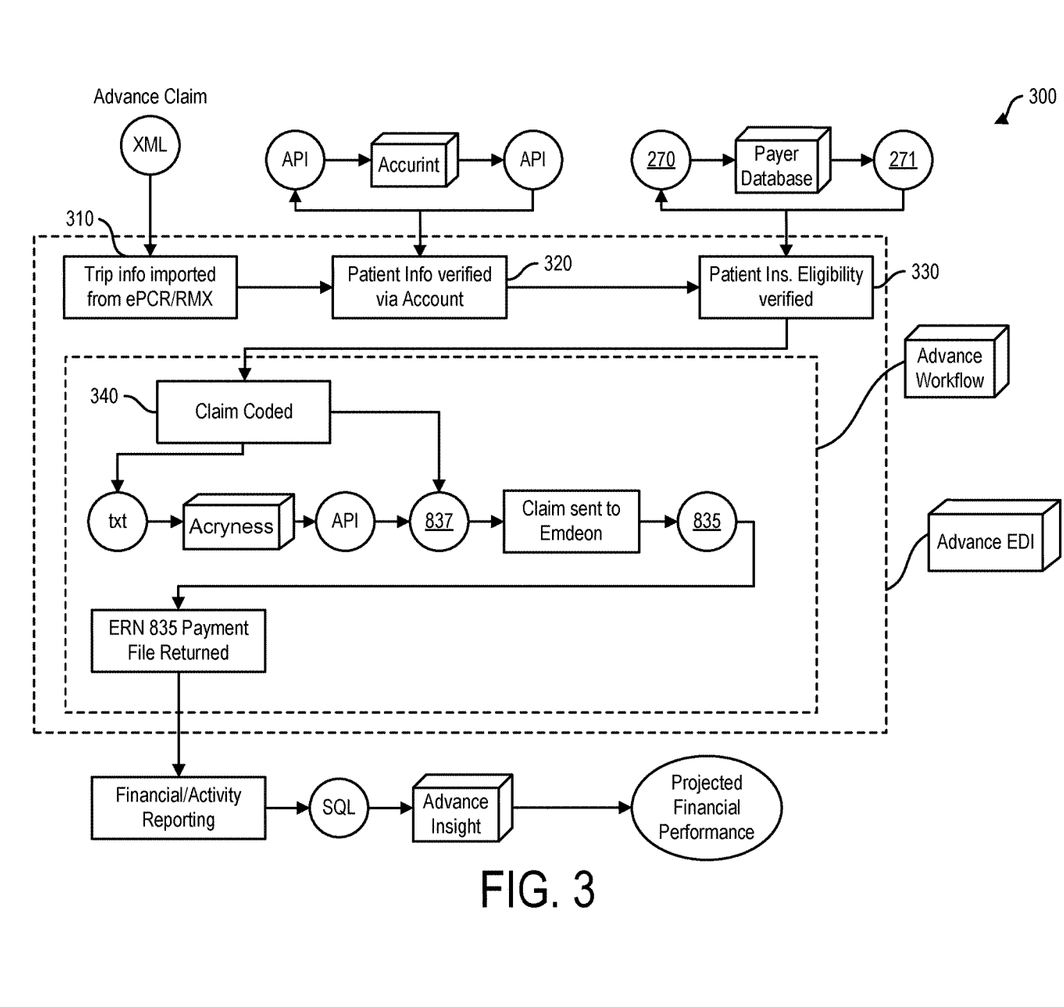
FIG. 3 shows a flow diagram illustrating some processing steps that can be associated with the claims module.
Figure 10:
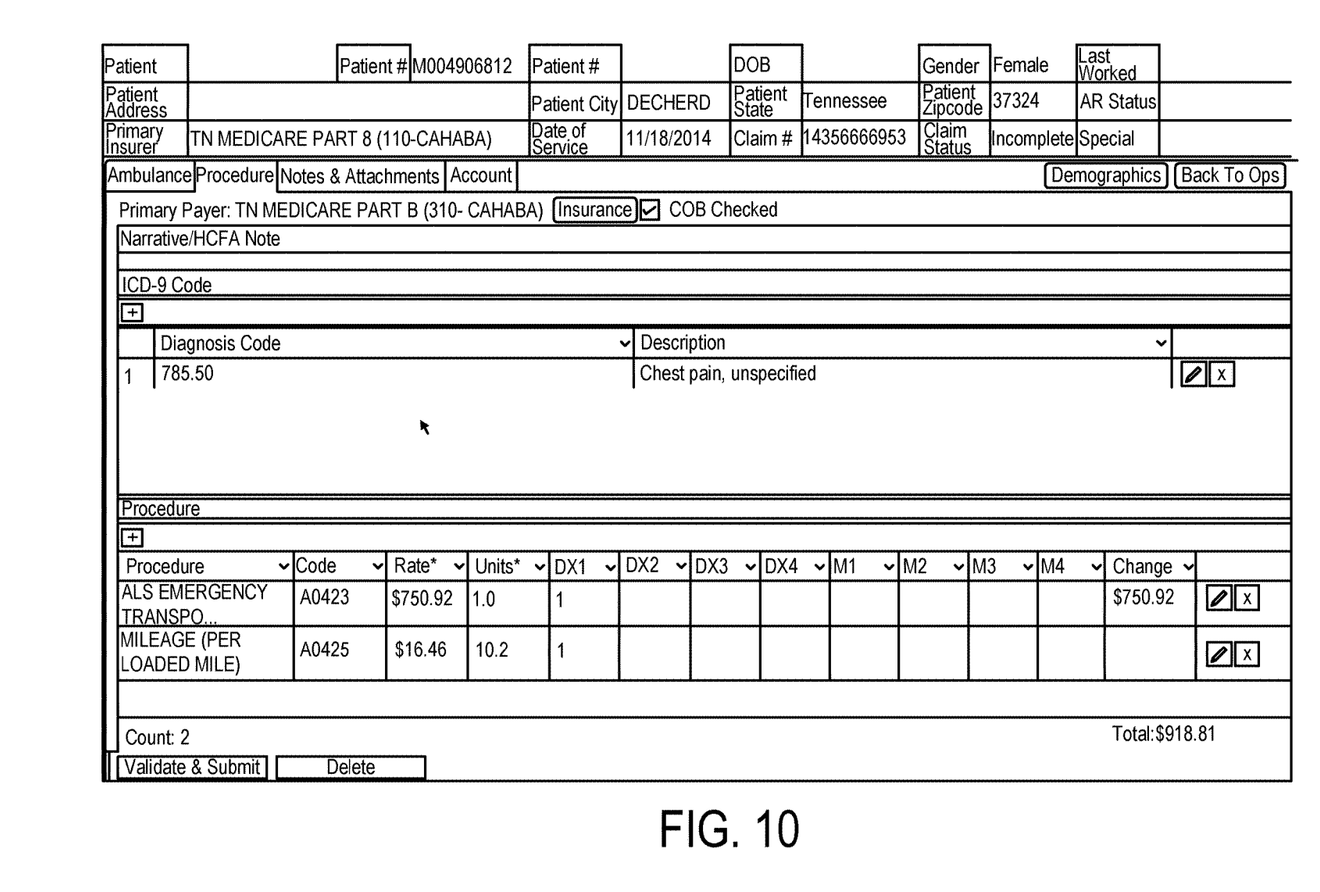
FIG. 10 shows an exemplary user interface for collecting claims information.

FIG. 3 is a process flow diagram 300 associated with the claims module 120. For example, at 310, information can be collected by the claims module 120, such as information related to an emergency medical service provided to a patient. FIG. 10 shows an exemplary user interface for collecting such claims information. For example, the information provided to the claims module 120 can be from information collected and/or generated by the dispatch module 110. At 320, the claims module 120 can collect information related to the patient (e.g., address, personal information, etc.), including patient information provided by another module of the EMS system 100 or a third party program. At 330, information related to the patient's insurance can be collected and verified. At 340, the collected information associated with the patient can be compiled into a claim and coded, such as for recording and storage purposes. The claim can be stored for future use and/or sent to other applications or modules, such as the income forecasting module 130. For example, claims created by the claims module 120 can assist with billing for emergency services provided to patients.

Figure 4:
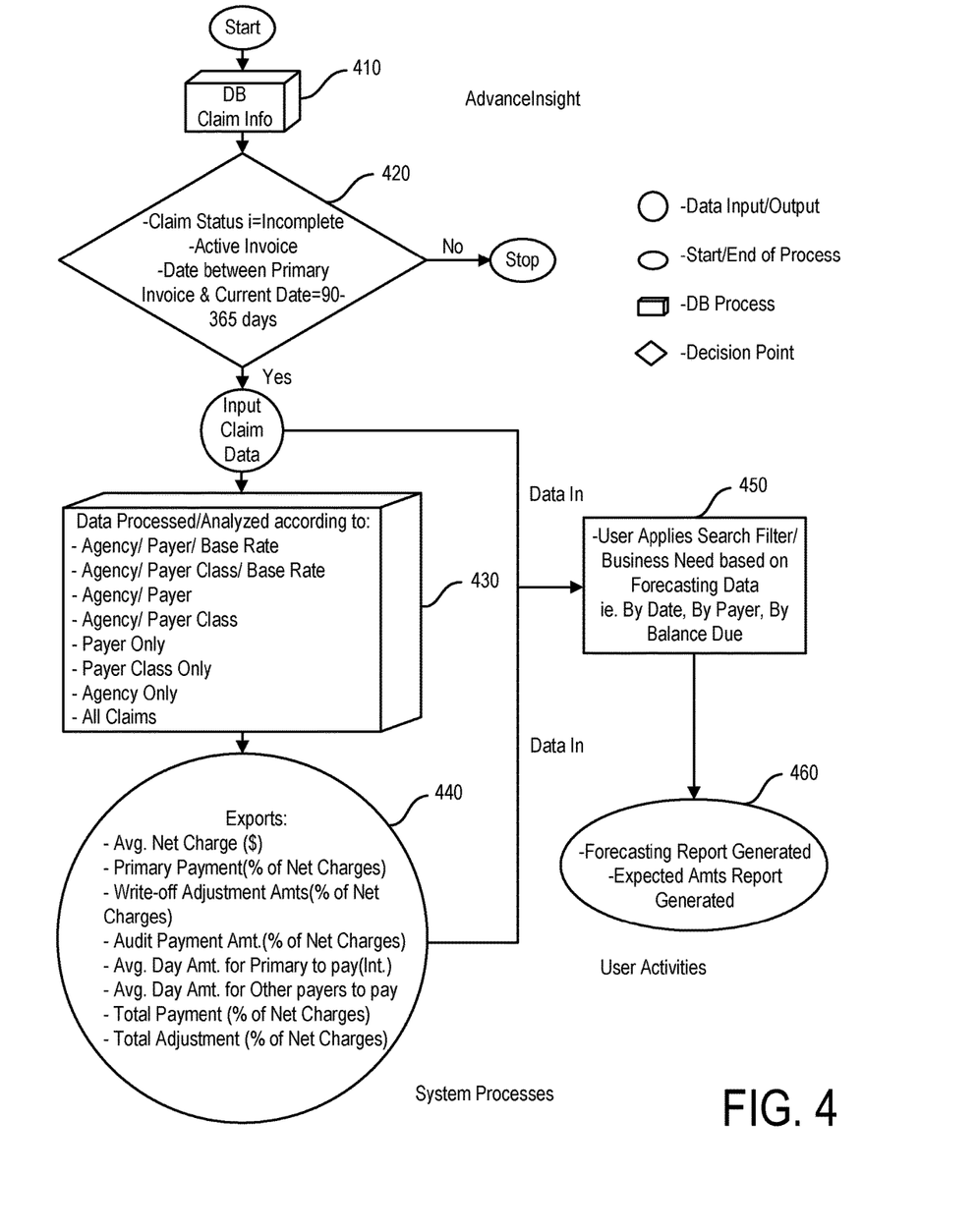
FIG. 4 shows a flow diagram illustrating some processing steps that can be associated with the forecasting module.

FIG. 4 illustrates a diagram showing a forecasting flow diagram 400 associated with the income forecast module 130. In some implementations, the income forecast module 130 can include a cloud-based modeling algorithm that can analyze data, such as historical data (e.g., claims billed, collected payments, outstanding payments, write-offs, etc.) any particular patient or groups of patients, and generate payment collection forecasting related to emergency medical services provided. For instance, the income forecast module can create a model of any particular patient, based on historical data for that particular patient or one or more other patients that have similar characteristics as the particular patient. The characteristics can include geographical information, age, gender, income status, EMS provided, and other characteristics. The payment collection forecasting can assist EMS providers with a more accurate estimation as to their financial performance, including expenses, revenue, etc.

For example, at 410, information can be collected by the income forecasting module 130, such as claim information related to a medical service provided to a patient. For example, the information collected by the income forecasting module 130 can be from a claim compiled in the dispatch claim module 120 and/or information from a database having ambulance claims for given medical providers (i.e., agency). Forecast percentages can then be calculated (e.g., percent of services billed expected to be received), such as using information collected at 410. At 420, a subset of data from the collected information can be selected to calculate one or more forecast percentages, including data related to claims that are incomplete, claims that are active (i.e., not deleted), and claims that have been approximately 60 to approximately 400 days since either the first invoice related to the claims was created or the date of service. As such, forecast percentages can be calculated for one or more claims that are at various stages within the billing and reimbursement process.

At 430, the selected subset of information can be forecasted according to one or more of a variety of forecasting models. For example, forecasting can be determined based on one or more forecasting models, each of which in turn can use one or more of the following payment procedures: an Agency/Payer/Base Procedure, Agency/Payer Class/Base Procedure, Agency/Payer, Agency/Payer Class Payer, Payer-Class, Agency, and All Claims model, which will be described in greater detail below. In addition, the forecasting models can provide a variety of accuracy, such as the agency/payer/base procedure model can be more accurate than the agency/payer class/base procedure model, which can be more accurate than the agency/payer model, and so on. The models can be attempted sequentially to find the model with the greatest accuracy that meets a pre-defined threshold of claims, such as if the agency/payer/base procedure model does not yield enough results to determine a forecast, the forecasting may be based on agency/payer class/base procedure, and so on.

At 440, based on the data collected and analyzed by the one or more forecasting models, a number of calculations can be made. For example, one or more of the following calculations can be made: average net charges, total payment (as a percent of actual charges), total adjustments/write-offs (as a percentage of actual charges), primary payment (as a percentage of actual charges), other non-primary payment (as a percentage of actual charges), average days to pay for a primary payer (i.e., integer), and average days to pay for non-primary/other payer (i.e., integer).

Figure 11:
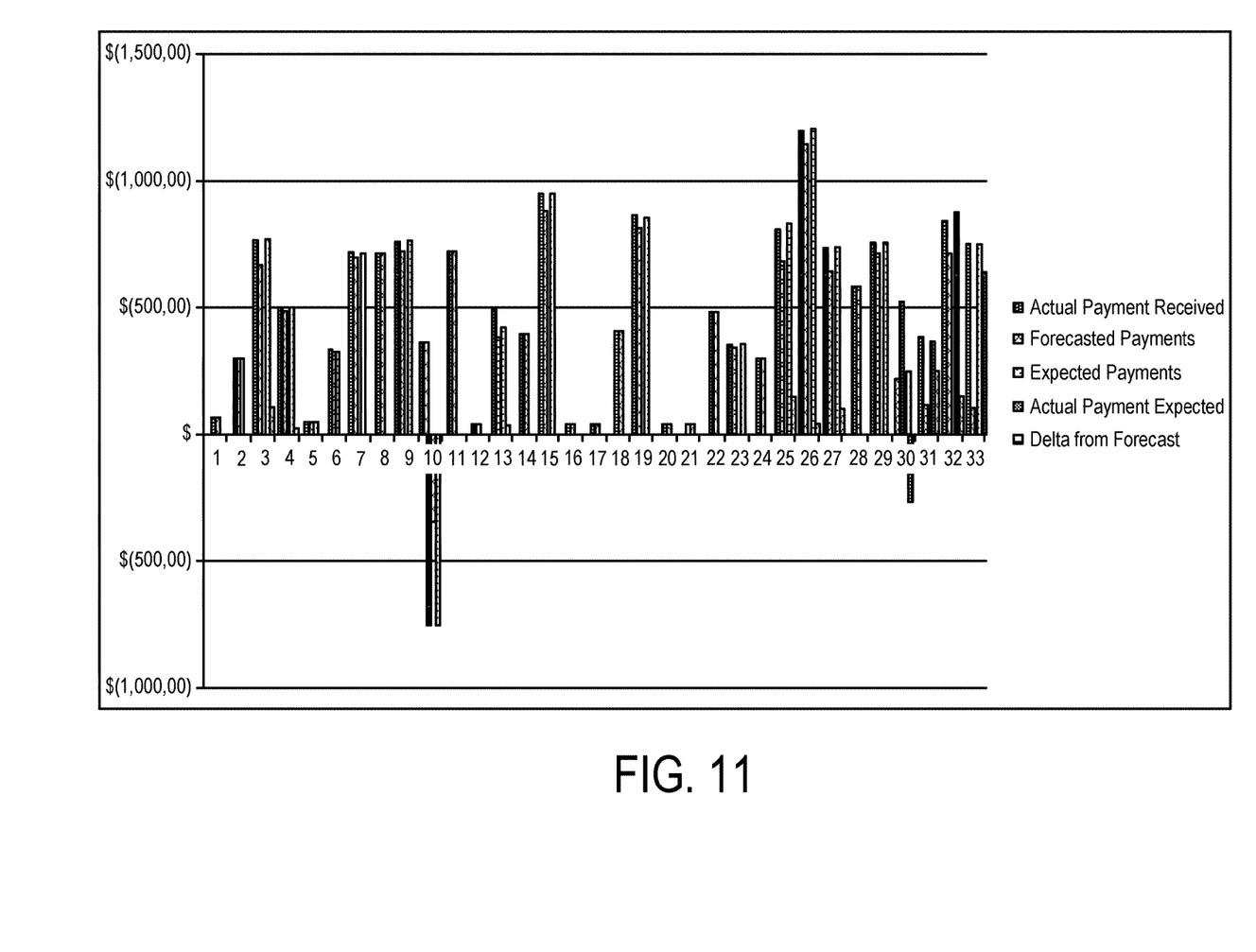
FIG. 11 shows an exemplary user interface that provides a graphical representation of actual versus expected versus forecasted income.

At 450, a user can define one or more claims to be forecasted, such as according to at least one of the following: all of the information available, by the date the service was provided, by the balance of the claim, by the payer, etc. In addition, at 460, the income forecasting module 130 can provide an output, such as an income forecasting report, which can include any of the information collected and/or calculated by the income forecasting module 130. For example, the output can show both the forecasted amounts, which can be theoretical using the forecasting models, and expected amounts, which can take into account actual payments, adjustments and/or write-offs that have already been applied to the claims. The forecasting outputs can be provided (e.g., displayed on a user-interface) in a variety of ways, including one or more of a graphical, spreadsheet, or illustrative form. FIG. 11 shows an exemplary user interface that provides a graphical representation of actual versus expected versus forecasted income, as generated by the forecasting module 130.

Some implementations of the income forecasting model 130 can calculate a forecasted payment assessment, which can include an amount of expected income based on claims that have been created. The forecasted payment assessment may not include payments already received. For example, if a claim has $1000 in charges and the primary payer averages payment of 50% of original charges of claims and other payers (e.g., secondary payers) average payment of 2% of the original charges of claims, then the forecasted payment for this claim can be $520.

In addition, an expected payment assessment can include remaining payments that are expected from a claim. The remaining payments that are expected from a claim can include a value of the projected accounts receivable of the claim. In addition, the expected payments can take into account payments already received. For example, a claim has $1000 in charges and the primary payer has paid $600. The secondary payer has been billed and has an average payment of 2% of the original charges. Therefore, the expected payment assessment for this claim can be $20.

Furthermore, an expected payment assessment can include one or more variables related to time of payment received or time of payment to-be received, such as expected or approximated times. By including a time variable to the expected payment assessment, a medical service provider can have a better understanding of when it can expect to be paid.

Additionally, actual payments received can include all payments received, such as payments received from all payers for one or more claims. The actual payments can be added to the expected payment assessment in order to derive a sum of the actual payments received for a claim plus expected payments. A delta forecast assessment can include a difference between forecasted payments and the sum of actual payments and expected results. A percent variance assessment can also be made from claim data. The percent variance assessment can include a percent variance between the forecasted payment and the sum of actual payments and expected results.

In some implementations, the delta forecast assessment can be used at least until a population of claims have been completed. A remaining forecast payment amount can represent an assumption about payments expected, but not yet collected, for the claims.

As discussed above, a variety of scenarios or forecasting models can be used to analyze claim data. For example, a first scenario can use all of the claims in the system except for those claims that have an incomplete status in order to determine a model. In addition or alternatively, a second scenario can use only the claims that have at least one payment in the system in order to determine the model. Either the first scenario or the second scenario can be run for a variety of time frames (e.g., hours, days, months), such as time frames before the time frame being modeled. For example, approximately 90-365 days, 120-365 days, 150-365 days, 180-365 days, and 210-365 days before the month being modeled can be used in a scenario.

The forecasting model can calculate the percent paid primary/other based on, for example, any one or more of a number of methods. The models can include Agency/Payer/Base Procedure, Agency/Payer Class/Base Procedure, Agency/Payer, Agency/PayerClass, Payer, PayerClass, Agency, and All Claims. For example, the Agency/Payer/Base Procedure model can look at claims for a provider (e.g., EMS Services, Inc), for a payer (e.g., California Medicare), for a base procedure (e.g. Basic Life Support Emergency Transport). Using this model, the forecasting model can predict with reasonable accuracy the expected payments, adjustments, etc., when the provider bills the payer for the base procedure. Failing to find a threshold of claims that match on agency/payer/base procedure, the model can proceed to look at all payers in the payer class (e.g., Medicare) instead of at a specific payer. In addition, the base procedure can be removed from the model and method checks can be made for Agency/Payer only—for example, EMS Services claims to Blue Cross Blue Shield (Agency/Payer), or EMS Services claims billed to any payer in the commercial insurance payer class (Agency/Payer Class). If the threshold cannot be met, agency can be removed from the model and it can search for claims from any provider submitted to payer (e.g., California Medicare), then payer class (e.g., Medicare payer class). As a last resort, the model can look at all claims within an agency or all claims in the database across agencies.

For example, if the forecasting model calculates x number of claims in one method (where x is equal to the defined threshold amount), it can use that method. If the model does not find the threshold amount of claims in a method, another method can be used. The various methods can be used in a sequential order. Either the first scenario or the second scenario can be used, along with a variety of thresholds amounts (x), in order to find the most accurate threshold amount.

Some results using the one forecasting model can provide results that are lower than a "best case" scenario, such as approximately 10% to approximately 15% lower, compared to another model. This result can be due to the inclusion of claims into the forecasted percentage when no payments have been collected, which can provide a realistic model since there can be several claims that have not been collected on.

In order to more accurately predict how the forecasting models reflect actual monies collected, snapshots of the forecasting models can be taken on a prescribed frequency and compared to the actual results. The prescribed frequency can be weekly, monthly, quarterly, annually, or any other regular or irregular frequency. The prescribed frequency can be pre-determined by the system, or configured by the system based on user input. Therefore, as more data is compiled and assessed using the forecasting models, the predictions can become increasingly more accurate over time. Information can also be collected when a claim is written off completely. For example, this information can be incorporated into the forecasting models in order to better compare the forecasted payments to actual payments received.

In some implementations, the forecasting module 130 can provide one or more of a summary related to payments received, forecasted payments, expected payments, a sum of the actual payments and the expected payments, and a delta from forecasted payments. The information provided in the summary can be based on any number of information related to one or more of expected payments, various forecasting (e.g., write-offs, etc.), charges for services, adjustments, payments received, amount initially billed, and details related to the claim (e.g., age of claim, insurance information, etc.). The summary information, and any information used to create the summary, can be displayed in a variety of forms, such as graphs, spreadsheets, illustrations, etc.

Figure 5:
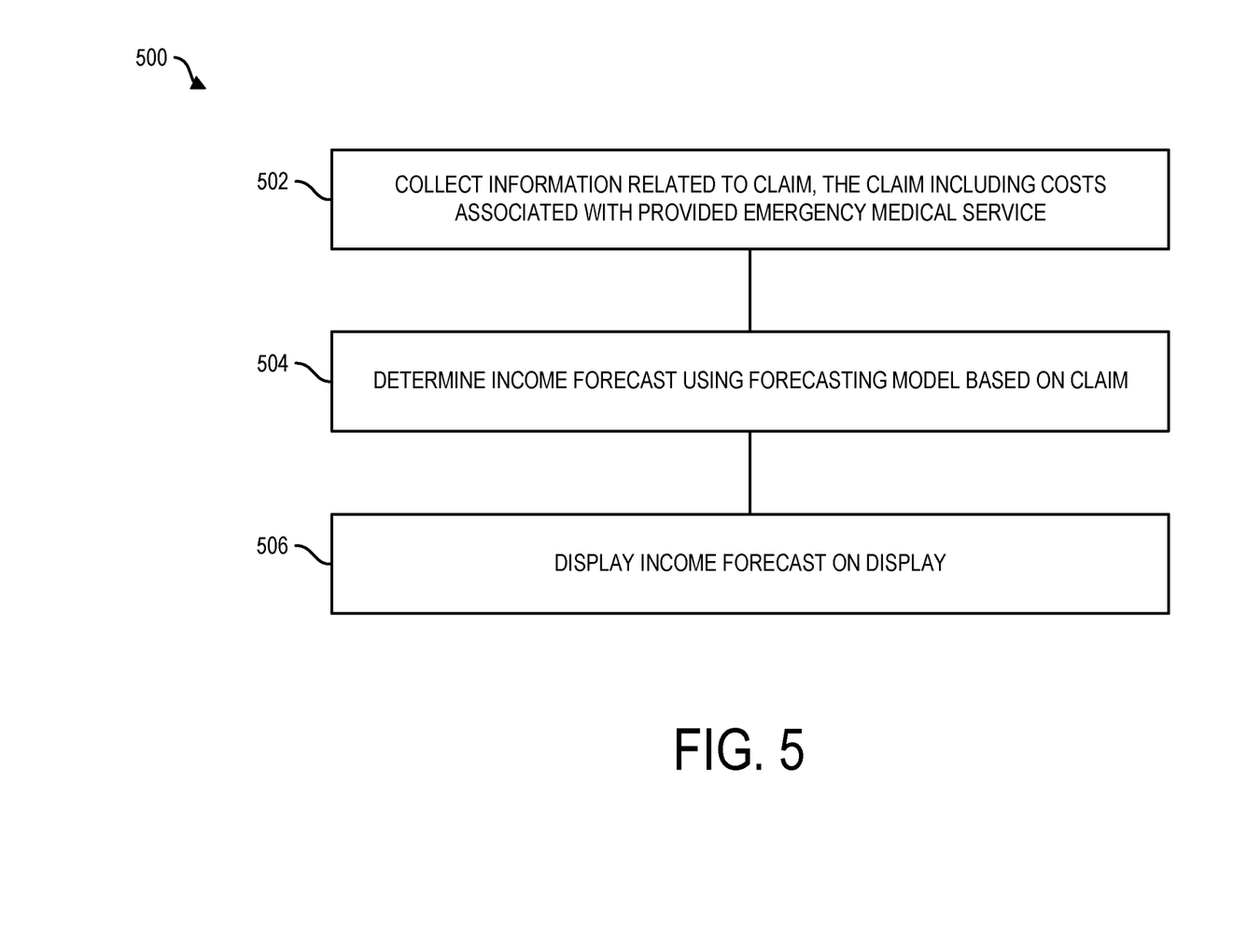
FIG. 5 shows a process flow diagram illustrating aspects of a method having one or more features consistent with implementations of the current subject matter.

FIG. 5 shows a process flow chart 500 illustrating features of a method consistent with one or more implementations of the current subject matter. It will be understood that other implementations may include or exclude certain features. At 504, information related to a claim is collected by the forecasting module, with the claim including costs associated with a provided emergency medical service. At 502, an income forecast is determined using a forecasting model based on the claim. At 506, the income forecast is displayed on a display.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, modules, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A method for processing emergency medical services (EMS) requests, the method comprising:
    storing information for a patient in interoperable EMS data format wherein the patient information is configured to be sent to, or received from, unrelated applications for additional processing, the unrelated application comprising clearinghouses and payors, the EMS data stored in a network connected database, and, comprising the patient's name, one or more medical conditions, at least one address, at least one insurer, and services data associated with each of one or more instances of EMS provided to the patient;
    providing, by at least one data processor, an indication of eligibility verification for the patient, the indication of eligibility based on at least one entry in the patient's EMS data;
    automatically assigning, by at least one data processor, at least one service unit to fulfill the EMS request, the assignment being transmitted to computing devices associated with the one or more service units via an electronic communication, the assignment based on capability and geo-location data associated with one or more service units, the geo-location data being obtained automatically from computing devices associated with the one or more service units;
    obtaining, by at least one data processor, an electronic status communication from the one or more service units assigned to provide EMS service;
    coding, by at least one data processor, a claim for the EMS dispatched to the patient, the claim being based at least in part on the status communication received from the one or more service units assigned to fulfill the EMS request, the status communication comprising at least one of medical conditions treated by the EMS service unit, and EMS data;
    selecting, by at least one data processor, a forecasting model from a number of forecasting models to forecast payment for the coded claim, the model selection made by sequentially attempting models and finding a model with appropriate accuracy that meets a pre-defined threshold of claims; and
    generating, by at least one data processor, a forecast for payment of the coded claim based on the selected forecasting model.

2. The method of claim 1, wherein the one or more of the following export items are calculated by applying the coded claim to the selected forecasting model: average net charges, total payment as a percent of actual charges, total adjustments/write-offs as a percentage of actual charges, primary payment as a percentage of actual charges, other non-primary payment as a percentage of actual charges, average days to pay for a primary payer, and average days to pay for nonprimary or other payer.

3. The method of claim 2, wherein the calculated export items are stored in the patent's EMS data.

4. The method of claim 3, wherein the generated forecast is further comprised of a theoretical forecast obtained by forecasting the coded claim with the selected forecasting model, and expected payment amount, which is based on calculated export items that are stored in the patient's EMS data.

5. The method of claim 4, further comprising comparing, by at least one data processor, the output of each of the two or more forecasting models with an actual result of a payment for the EMS to the patient.

6. The method of claim 5, wherein the comparison by the forecasting module is executed at a prescribed frequency.

7. The method of claim 1, wherein the geolocation data is provided by an external geolocation service.

8. A non-transitory computer program product storing instructions that, when executed by at least one programmable processor, cause the at least one programmable processor to perform operations comprising:
    store information for a patient in interoperable EMS data format wherein the patient information is configured to be sent to, or received from, unrelated applications for additional processing, the unrelated application comprising clearinghouses and payors, the EMS data stored in a network connected database, and, comprising the patient's name, one or more medical conditions, at least one address, at least one insurer, and services data associated with each of one or more instances of EMS provided to the patient;
    provide an indication of eligibility verification for the patient, the indication of eligibility based on at least one entry in the patient's EMS data;
    automatically assign at least one service unit to fulfill the EMS request, the assignment being transmitted to computing devices associated with the one or more service units via an electronic communication, the assignment based on capability and geo-location data associated with one or more service units, the geo-location data being obtained automatically from computing devices associated with the one or more service units;

obtain an electronic status communication from the one or more service units assigned to provide EMS service;

code a claim for the EMS dispatched to the patient, the claim being based at least in part on the status communication received from the one or more service units assigned to fulfill the EMS request, the status communication comprising at least one of medical conditions treated by the EMS service unit, and EMS data;

select a forecasting model from a number of forecasting models to forecast payment for the coded claim, the model selection made by sequentially attempting models and finding a model with appropriate accuracy that meets a pre-defined threshold of claims; and generate a forecast for payment of the coded claim based on the selected forecasting model.

9. A system comprising:

at least one programmable processor; and a machine-readable medium storing instructions that, when executed by the at least one processor, cause the at least one programmable processor to perform operations comprising:

storing information for a patient in interoperable EMS data format wherein the patient information is configured to be sent to, or received from, unrelated applications for additional processing, the unrelated application comprising clearinghouses and payors, the EMS data stored in a network connected database, and, comprising the patient's name, one or more medical conditions, at least one address, at least one insurer, and services data associated with each of one or more instances of EMS provided to the patient;

providing an indication of eligibility verification for the patient, the indication of eligibility based on at least one entry in the patient's EMS data;

automatically assigning at least one service unit to fulfill the EMS request, the assignment being transmitted to computing devices associated with the one or more service units via an electronic communication, the assignment based on capability and geo-location data associated with one or more service units, the geo-location data being obtained automatically from computing devices associated with the one or more service units;

obtaining an electronic status communication from the one or more service units assigned to provide EMS service;

coding a claim for the EMS dispatched to the patient, the claim being based at least in part on the status communication received from the one or more service units assigned to fulfill the EMS request, the status communication comprising at least one of medical conditions treated by the EMS service unit, and EMS data;

selecting a forecasting model from a number of forecasting models to forecast payment for the coded claim, the model selection made by sequentially attempting models and finding a model with appropriate accuracy that meets a pre-defined threshold of claims; and generating a forecast for payment of the coded claim based on the selected forecasting model.

* * * * *